United States Patent
Stutz

(10) Patent No.: US 9,685,265 B2
(45) Date of Patent: Jun. 20, 2017

(54) WEARABLE MAGNET HOUSING

(71) Applicant: MAGNETACTICAL LLC, South Jordan, UT (US)

(72) Inventor: Devin Fredrickson Stutz, South Jordan, UT (US)

(73) Assignee: Magnetactical LLC, South Jordan, UT (US)

( * ) Notice: Subject to any disclaimer, the term of this patent is extended or adjusted under 35 U.S.C. 154(b) by 87 days.

(21) Appl. No.: 14/502,696

(22) Filed: Sep. 30, 2014

(65) Prior Publication Data

US 2015/0107061 A1    Apr. 23, 2015

Related U.S. Application Data

(60) Provisional application No. 61/892,360, filed on Oct. 17, 2013, provisional application No. 62/020,198, filed on Jul. 2, 2014.

(51) Int. Cl.
*A44B 1/04* (2006.01)
*H01F 7/02* (2006.01)
*A61N 2/06* (2006.01)

(52) U.S. Cl.
CPC ............ *H01F 7/0294* (2013.01); *A61N 2/06* (2013.01); *Y10T 24/32* (2015.01)

(58) Field of Classification Search
CPC ... Y10T 24/32; Y10S 211/01; A44D 2203/00; A45F 5/00; A45F 5/02; A45F 5/021; H01F 7/0252
See application file for complete search history.

(56) References Cited

U.S. PATENT DOCUMENTS

| | | | | | |
|---|---|---|---|---|---|
| 3,063,118 | A | * | 11/1962 | Salter | A44B 11/258 223/109 A |
| 3,208,123 | A | * | 9/1965 | Koos | A44B 11/001 224/163 |
| 3,755,857 | A | * | 9/1973 | Simoneaux | A44C 5/0046 132/331 |
| 5,196,818 | A | * | 3/1993 | Anderson | A45F 5/00 223/109 A |
| 5,333,767 | A | * | 8/1994 | Anderson | A45F 5/00 223/109 A |
| 7,677,722 | B1 | * | 3/2010 | Mednick | A45F 5/02 351/111 |
| 8,550,235 | B2 | * | 10/2013 | Suderman | F16B 7/0433 198/690.1 |

(Continued)

OTHER PUBLICATIONS

"Magnetic Belt Clip." Magnogrip, Inc. Getfused CMS. n.d. Web. Available at least as early as Aug. 27, 2014, 2 pages. Available at <http://www.magnogrip.com/index.cfm?pid=10455>.

*Primary Examiner* — Robert J Sandy
*Assistant Examiner* — Matthew Sullivan
(74) *Attorney, Agent, or Firm* — Workman Nydegger

(57) ABSTRACT

Wearable housings are configured in size and shape to be securely attached to a strap, such as a belt, suspender, backpack strap, rifle strap, shoulder bag strap, vest, carrier, or other strap with one or more clasping members. One or more magnets are positioned within the substantially hollow receptacle area(s) of the wearable housing. The magnet(s) have sufficient holding force to securely hold a handgun or other item against the wearable housing for ready access.

18 Claims, 10 Drawing Sheets

(56) References Cited

U.S. PATENT DOCUMENTS

| | | | |
|---|---|---|---|
| 2012/0178547 A1* | 7/2012 | Famulari | A45F 5/021 473/282 |
| 2013/0097817 A1* | 4/2013 | Hayton | A44B 11/06 24/303 |
| 2015/0013205 A1* | 1/2015 | Franklin | A45F 5/021 42/94 |

\* cited by examiner

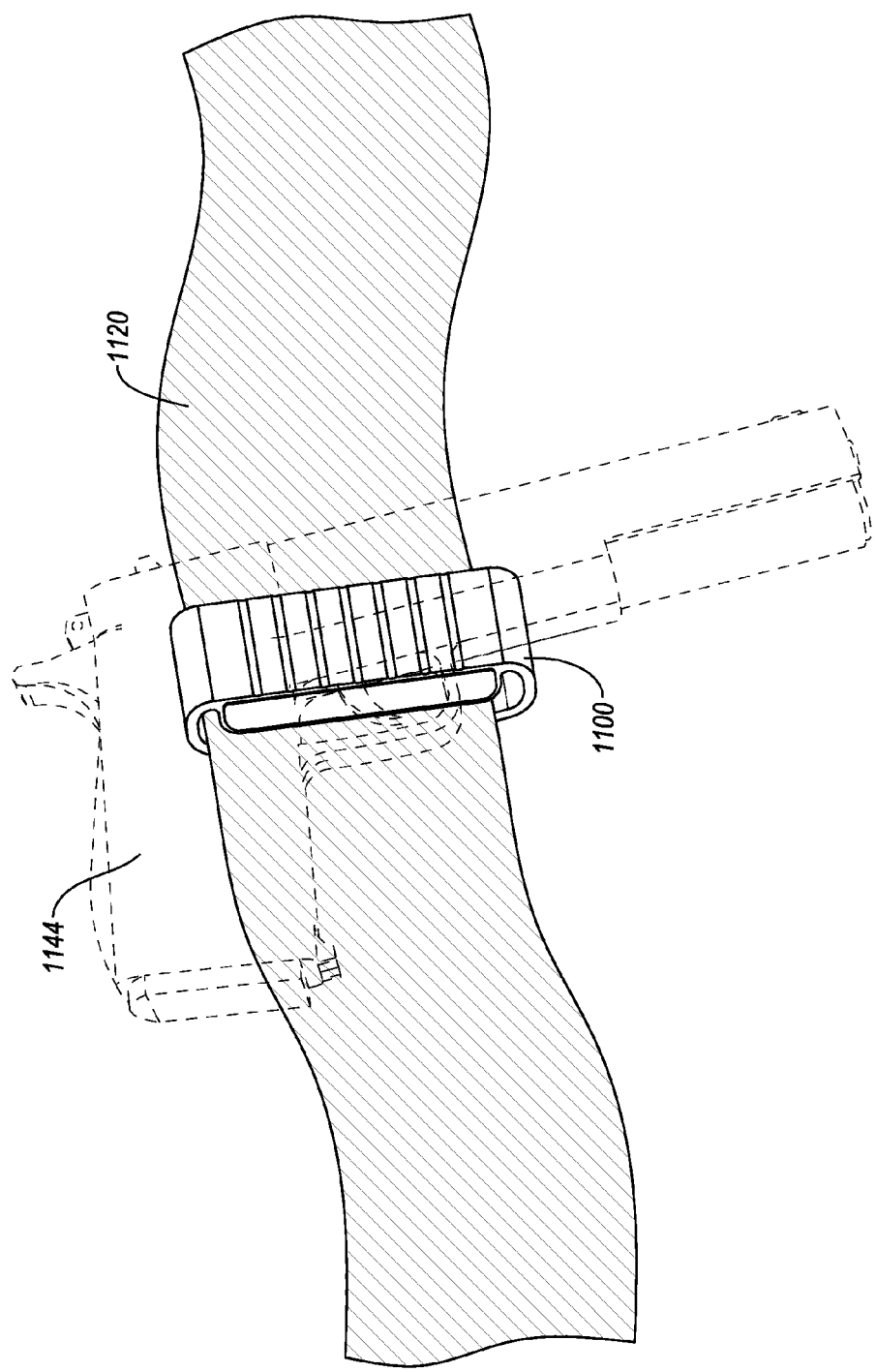

WEARABLE MAGNET HOUSING

CROSS-REFERENCE TO RELATED APPLICATIONS

This application claims the benefit of U.S. Provisional Patent Application Nos. 61/892,360, filed on Oct. 17, 2013, and 62/020,198, filed on Jul. 2, 2014, both of which are hereby incorporated by reference in their entireties.

FIELD OF THE DISCLOSURE

The present invention generally relates to wearable clips or housings configured for holding one or more magnets and that are configured to be selectably connected to belts or other straps like structures.

BACKGROUND

Many utility items such as flashlights, knives, guns, and other handheld tools provide utility requiring manual manipulation and accessibility for proper use and function. In some instances, an item may need to be placed down or placed away for a moment, in order for a user to accomplish another task or use his/her hands for another purpose. Easy retrieval of many of these items is, therefore, desirable. As such, it is desirable that such items be placed or positioned in a location that is easily accessible, such as on the person that is actually utilizing the tool(s).

To accomplish the foregoing, many items can be tied or secured to a wearable strap, such as a belt. In other situations, a container or holster is used. While such approaches are beneficial, there is an ongoing need for improved products to aid in the containment or securing of tools and other items in a readily accessible manner.

BRIEF SUMMARY

Embodiments of the present disclosure include wearable housings or clips that are configured in size and shape to be attached to a strap, such as a belt, suspender, backpack strap, rifle strap, shoulder bag strap, vest, carrier, or other strap-like structure.

Certain embodiments include one or more magnets positioned within a substantially hollow receptacle or housing that is configured to be attached directly to a belt or other strap-like structure. The magnet(s) and/or substantially hollow receptacle area(s) may be configured in size and shape so that the magnet(s) securely fit within the substantially hollow receptacle area(s). Certain embodiments include one or more support fins that aid in positioning of a magnet within a substantially hollow receptacle area.

Certain embodiments include one or more clasping members that are configured in size and shape to connect the wearable housing to the belt or strap-like structures. The clasping members can be configured out of a flexibly resilient material to apply a desirable friction force to the belt or strap positioned between the clasp(s) and the clip housing.

In certain embodiments, an exterior surface of an outer wall may include a textured surface. A textured surface may advantageously provide friction and prevent slipping of objects against the exterior surface of the outer wall, such as when a utility item (e.g., tool, knife, handgun, flashlight, etc.) is magnetically secured against the exterior surface of the outer wall.

Other aspects and advantages of the invention will be apparent from the following description and the appended claims. The various characteristics described above, as well as other features, will be readily apparent to those skilled in the art upon reading the following detailed description, and by referring to the accompanying drawings. This summary is therefore not intended to identify key or essential features of the claimed subject matter, nor is it intended to be used as an aid in limiting the scope of the claims.

BRIEF DESCRIPTION OF THE DRAWINGS

In order to describe various features and concepts of the present disclosure, a more particular description of certain subject matter will be rendered by reference to specific embodiments which are illustrated in the appended drawings. While each embodiment contemplated hereby may not be drawn to scale, at least some of the appended drawings may be drawn to scale. Understanding that these drawings depict just some example embodiments and are not to be considered to be limiting in scope, various embodiments will be described and explained with additional specificity and detail through the use of the accompanying drawings in which:

FIG. 11 illustrates a wearable housing connected to a strap and a utility item magnetically associated with the wearable housing and secured in place against the wearable housing.

DETAILED DESCRIPTION

Figure 1A:
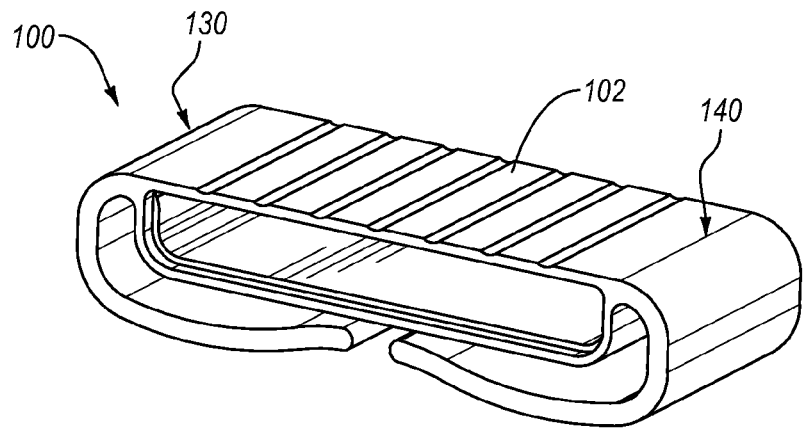
FIGS. 1A-1F illustrates multiple views of one embodiment of a wearable housing of the present disclosure.

The following is directed to various embodiments of the disclosure. The embodiments disclosed should not be interpreted, or otherwise used, to limit the scope of the disclosure including the claims. In addition, those having ordinary skill in the art will appreciate that the following description has broad application, and the discussion of any embodiment is not intended to suggest that the scope of the disclosure, including the claims, is limited to that embodiment.

Certain terms are used throughout the following description and claims to refer to particular features or components. As those having ordinary skill in the art will appreciate, different persons may refer to the same feature or component by different names. This document does not intend to distinguish between components or features that differ in name but not function. Certain features and components herein may be shown exaggerated in scale or in somewhat schematic form and some details of conventional elements may not be shown or described in interest of clarity and conciseness. As used in the specification and the appended claims, the singular forms "a," "an," and "the" are intended to include the plural forms as well, unless the context clearly indicates otherwise.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' preferred, 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment.

The term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

As used herein the term "strap" and "belt" are used interchangeably. It will be appreciated, however, that these terms can also include structures, such as, flaps, pockets, cords and other structures that are configured in size and shape to pass through the clasping structures and loops formed by the wearable housing structures of the invention.

FIGS. 1A-1G illustrate an embodiment of a wearable housing of the present disclosure, with FIG. 1A showing a isometric view, 1B showing a front view, 1C showing a back view, 1D showing a top view, 1E showing a bottom view and 1F showing a side view, wherein each of the two opposing sides are the same.

In these figures, a wearable housing 100 includes an outer wall 102 and an inner wall 104. The outer wall 102 and the inner wall 104 may be separated a predetermined distance from each other (e.g., a distance in a range of between about 0.125 inches and about 0.5 inches, or greater than 0.5 inches in some embodiments). The outer wall 102 and the inner wall are also connected by a first sidewall 106 and a second sidewall 108 by a distance within a range of between about 0.5 inches and about 3 inches, or even more than 3 inches.

In the embodiment shown, the outer wall 102, the inner wall 104, the first sidewall 106, and the second sidewall 108 connect to form a substantially hollow receptacle area 110 with a rectangular cuboid shape having angles that are approximately 90 degrees (i.e., are substantially right angles). In other embodiments, the outer wall 102, the inner wall 104, the first sidewall 106, and the second sidewall 108 may connect to form a substantially hollow receptacle area 110 with a different shape and/or with different vertex angles, such as a cube, rhombohedron, or parallelepiped.

As shown in FIGS. 1A through 1G, the outer wall 102, the inner wall 104, the first sidewall 106, and the second sidewall 108 may have faces or surfaces that are substantially flat. In other embodiments, the outer wall 102, the inner wall 104, the first sidewall 106, and/or the second sidewall 108 may include additional vertices, such that they connect to form a substantially hollow receptacle area 110 with a polyhedron shape that is non-cuboid, non-rhombohedron, and non-parallelepiped. For example, the outer wall 102, the inner wall 104, the first sidewall 106, and the second sidewall 108 may connect to form a substantially hollow receptacle area 110 that is a convex, concave, symmetrical, and/or asymmetrical polyhedron shape or other complex shape (not presently shown).

In other embodiments, the inner wall 104, the first sidewall 106, and/or the second sidewall 108 may be curved or may include a curved portion, such that the outer wall 102, the inner wall 104, the first sidewall 106, and the second sidewall 108 do not form hard or identifiable edges at every connection. For example, the outer wall 102, the inner wall 104, the first sidewall 106, and the second sidewall 108 may connect to form a substantially hollow receptacle area 110 that is substantially ellipsoid in shape and/or that has an elliptical shaped cross section or partially elliptical shaped cross section.

The wearable housing 100 may be manufactured out of plastic, metal, ceramic, fabric, or any other material or combination of materials configured in size and shape to include a substantially hollow receptacle area 110 capable of housing one or more magnets of sufficient size and strength to accommodate a user's needs and preferences.

The wearable housing may be constructed to be substantially solid (i.e., the walls and other members of the housing are solid pieces of material), or may be constructed as a framework or skeleton design (i.e., walls and other members of the housing are framings or outlines with striated, webbed, or other shaped openings within).

The substantially hollow receptacle area 110 may be hollow, such that no other portions of the wearable housing 100 project into the open space of the substantially hollow receptacle area 110. In other embodiments, the substantially hollow receptacle area may not be completely hollow. For example, support structures, partitions, projections, mold production artifacts or other objects may occupy a portion of the space within the substantially hollow receptacle area 110, such as the fins described below and as shown in at least FIGS. 2A-2C.

Figure 1B:
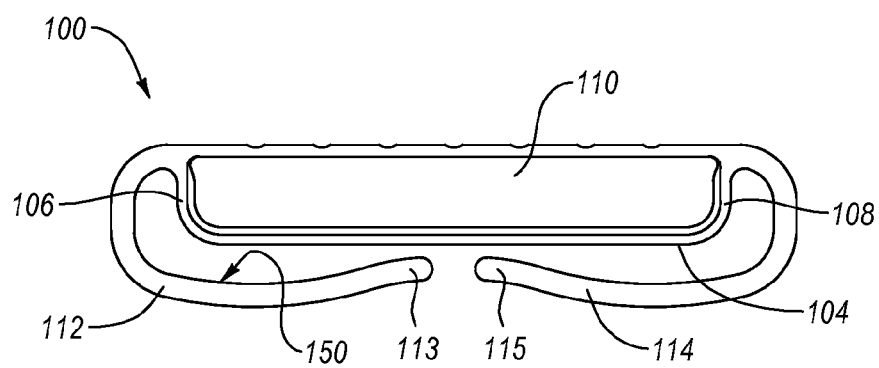
Figure 1C:
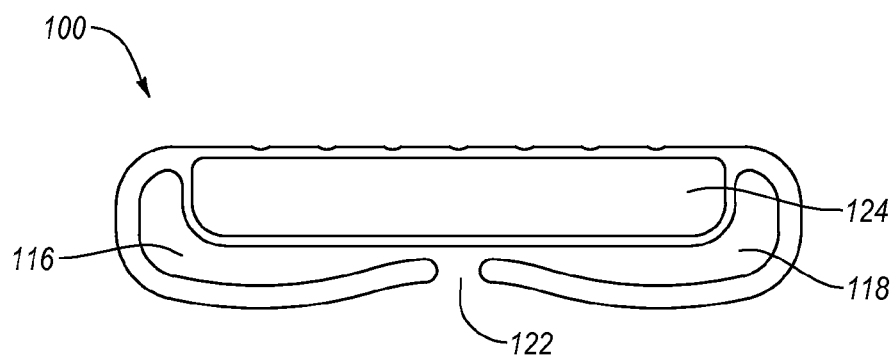
Figure 1D:
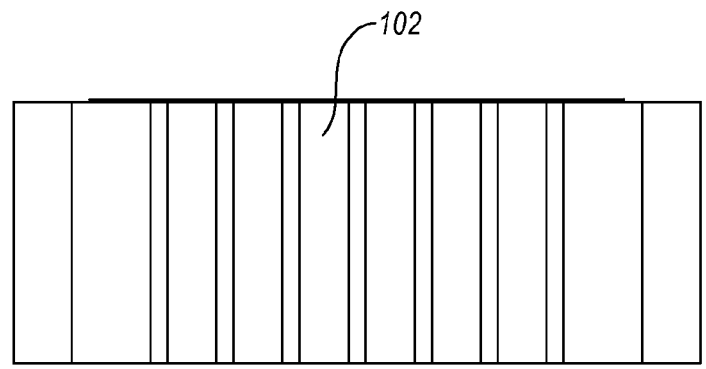
Figure 1E:
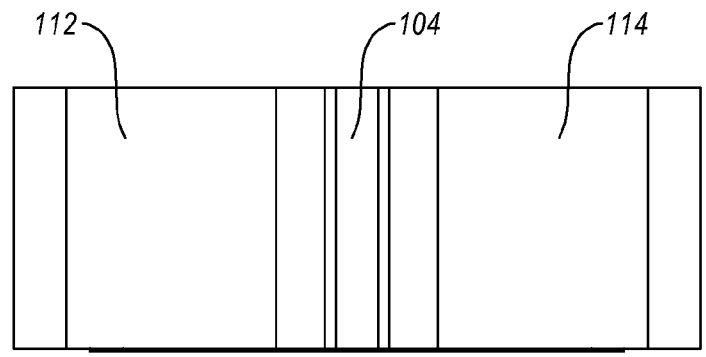
Figure 1F:
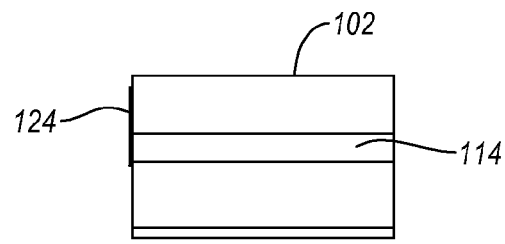

In the embodiment of FIGS. 1A-1C, the outer wall 102 includes corresponding exterior and interior surfaces (e.g., a surface that is exterior to the substantially hollow receptacle area 110 and a surface that is interior to the substantially hollow receptacle area 110) and the inner wall 104 includes a corresponding interior and an exterior surface.

The embodiment shown in FIGS. 1A through 1G also includes a first clasping member 112 and a second clasping member 114. In some embodiments, the first clasping member 112 is disposed at a first end of the outer wall 102, and extends around the inner wall 104 to a terminating end 113 adjacent to the exterior surface of the inner wall 104. Similarly, the second clasping member 114 is disposed at a second end of the outer wall 102, and extends around the inner wall 104 to a terminating end 115 adjacent to the exterior surface of the inner wall 104. The first clasping member 112 forms a first slot 116 defined by the area between the first clasping member 112 and the exterior surface of the inner wall 104, and the second clasping member 114 forms a second slot 118 defined by the area between the second clasping member 114 and the exterior surface of the inner wall 104.

In the embodiment shown in FIGS. 1A-1G, the first clasping member 112 and the second clasping member 114 are disposed from or protrude from first and second ends of the outer wall, respectively. In other embodiments, the clasping members may be disposed from or protrude from other areas of the wearable housing (see, e.g., FIG. 8 and FIGS. 9A-9C). For example, the first clasping member 112 may extend away from an area proximate the first end 130 of the outer wall 102 or from the first sidewall 106 or from both before extending to the terminal point 113 adjacent to the exterior surface of the inner wall 104. Likewise, the second clasping member 114 may be disposed from an area proximate the second end 140 of the outer wall 102 or from the second sidewall 108 or from both before extending to the terminal point 115 adjacent to the exterior surface of the inner wall 104.

As illustrated by the embodiment shown in FIGS. 1A-1G, a clasping member may also have one or more curved or arcuate portions. For example, a clasping member 112,114 may include one or more portions 150 that curve out or away from the exterior surface of the inner wall 104 and/or one or more portions that curve in or toward the exterior surface of the inner wall 104.

In some embodiments, the housing only has a single clasping member. In other embodiments, three, four, or more clasping members are included, such that there may be a plurality of clasping members disposed from a first end of the outer wall and/or from the first sidewall and/or a plurality of clasping members disposed from a second end of the outer wall and/or from the second sidewall.

In the embodiment shown in FIGS. 1A-1G, the first clasping member 112 and the second clasping member 114 have widths that are substantially the same as the widths of the outer wall 102 and the inner wall 104. This width can vary in size to accommodate different needs and preferences. In some embodiments, the width is within a range of about 0.5 inches and 2 inches. In other embodiments, the width is less than 0.5 inches or more than 2 inches.

In yet embodiments, the widths of the outer wall 102, the inner wall 104, the first clasping member 112, and the second clasping member 114 are not the same. For example, the widths of the first clasping member 112 and/or the second clasping member 114 may be wider or smaller than the outer wall 102 and/or inner wall 104. Additionally, or alternatively, the widths of the first clasping member 112 and/or the second clasping member 114 may be non-uniform and/or may taper in one direction or the other. The outer wall 102 and the inner wall 104 may also have different widths, and they may be non-uniform and/or may taper in one direction or the other.

In the embodiment shown in FIGS. 1A-1G, the first clasping member 112 and the second clasping member 114 have terminating ends 113 and 115 that do not coincide or abut one another, leaving a gap 122. In other embodiments, discussed in more detail below, the gap 122 may be narrower or wider (see, e.g., FIGS. 5 and 6). Alternatively, the clasping members may form an enclosed loop, effectively omitting any gap (see, e.g., FIG. 7).

Figure 1G:
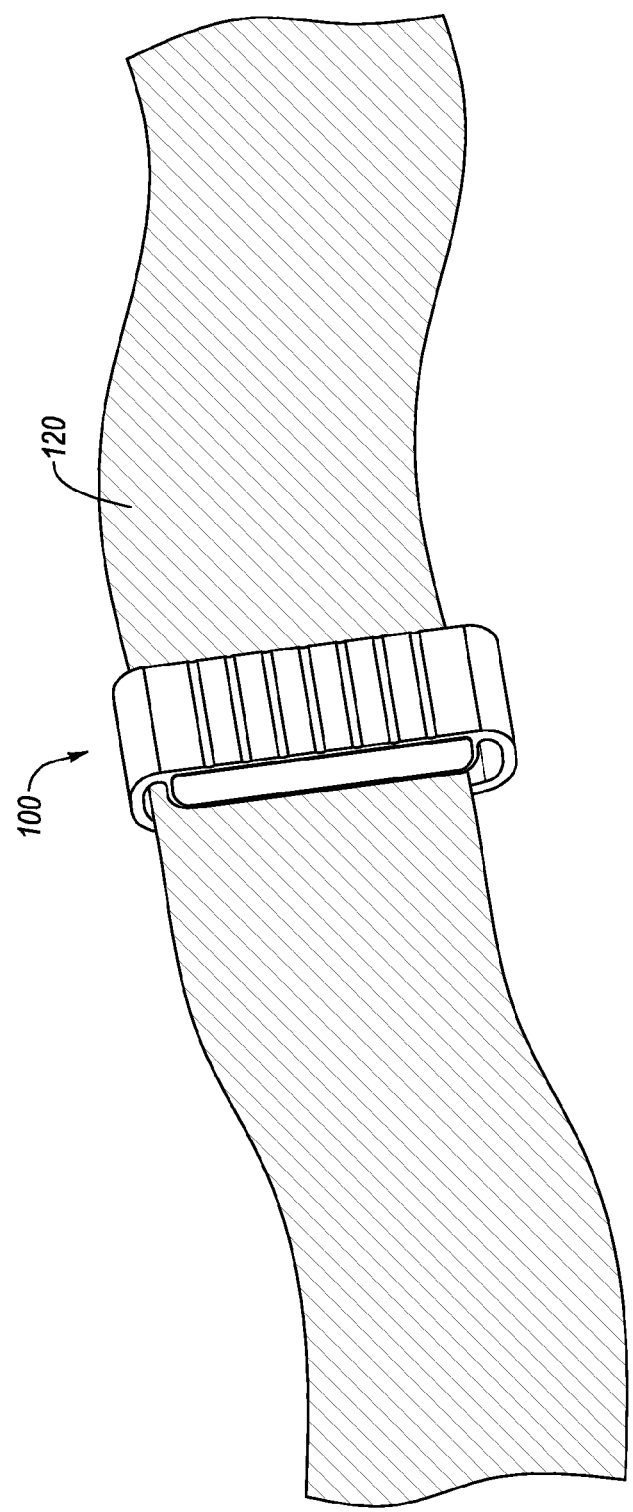
FIG. 1G illustrates a wearable housing attached to a strap.

FIG. 1G illustrates that embodiments of the present disclosure may be configured for attachment to or association with a strap 120 or strap like structure. A strap 120 may be a wearable strap, such as a belt (e.g., tactical, military, law-enforcement, utility, casual), suspender, shoulder strap, backpack strap, rifle strap, vest, carrier, or any other form of material with at least a portion including a substantially flat cross section. Additionally, or alternatively, the strap 120 may be constructed in a rope or cord-like fashion, such that a cross-section is not necessarily flat or substantially flat. The strap can also be a partial strap, such as a pocket. The wearable housing 100 may be attached or associated with a strap 120 by positioning the strap into the first slot 116 and/or second slot 118 of the wearable housing 100.

In some embodiments, the clasping members may be configured to secure the wearable housing 100 firmly in place against the strap 120 to prevent lateral and vertical movement along the strap 120. For example, the clasping members 112, 114 may be configured such that the first slot 116 and second slot 118 have one or more portions that are narrower than the thickness of a strap 120, thereby being configured to flex against and secure a strap 120 when the wearable housing 100 is positioned on a strap 120. The spacing between the exterior surface of the inner wall 104 and the clasping members 112 and/or 114 can vary to accommodate different needs and preferences. In some embodiments, the clasping members are configured to be positioned between about 0.03125 of an inch and about 0.25 inches from the exterior surface of the inner wall. The flexible characteristics of the clasping members can also vary (e.g., resulting from different materials and material thicknesses of the clasping members). The thickness of the clasping members can be, in some embodiments, between about 0.03125 of an inch and about 0.25 inches.

In alternative embodiments, the clasping members may be configured to allow unrestricted lateral movement along the strap 120, such that the wearable housing 100 is freely slidable along the strap 120 into different positions along the strap 120. Additionally, or alternatively, the clasping members may be configured to allow vertical movement along the strap 120. In some embodiments (such as those embodiments including only one clasping member), a wearable housing may be connected to a strap with only one clasping member. For example, the clasping members 112,114 may be configured to not flex against a strap 120 or to flex against a strap 120 gently enough to allow movement of the housing 100 along the strap 120.

In some embodiments, a wearable housing 100 includes a back wall 124 connected to the first side wall 106, the second sidewall 108, the outer wall 102, and the inner wall 104, thereby further enclosing the substantially hollow receptacle area 110 at a first end of the substantially hollow receptacle area 110. The back wall 124 may be substantially flat, as in FIGS. 1A-1G, or may include additional vertices and/or include curved portions.

The outer wall 102 may include a textured pattern, such as the grooved pattern shown in at least FIGS. 1A-1G. A textured pattern may be formed by one or more grooves or other indentations formed into the exterior surface of the outer wall 102, by one or more projections formed on the exterior surface of the outer wall 102, or by a combination of grooves/indentations and projections. The textured pattern may be isotropic or anisotropic.

In some embodiments, such as those shown in at least FIGS. 1A-1G, the textured pattern may be disposed in a transverse direction (i.e., grooves or projections or both run transversely). In other embodiments, the textured pattern may be disposed longitudinally, diagonally, or in a combination of two or more directions, or with portions that run in one direction and other portions that run in another direction. In some embodiments, the textured pattern is a diamond, honeycomb, radial, or other complex pattern (see, e.g., FIGS. 4A and 4B). One of skill in the art will note that any combination of these patterns may be used, such that the outer wall 102 may be uniformly or non-uniformly textured, and that some, all, or none of the outer wall 102 may exhibit a textured pattern. The texturing can help prevent or resist sliding of a tool positioned against the surface.

Figure 2A:
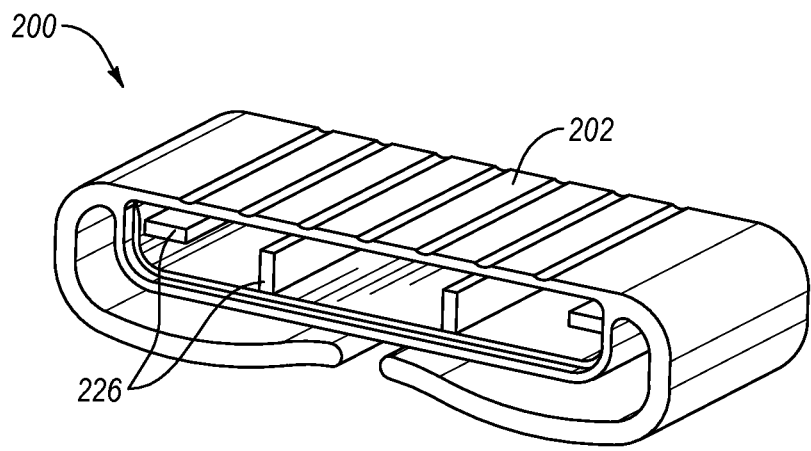
FIGS. 2A and 2B illustrate an embodiment of a wearable housing including support fins.
Figure 2B:
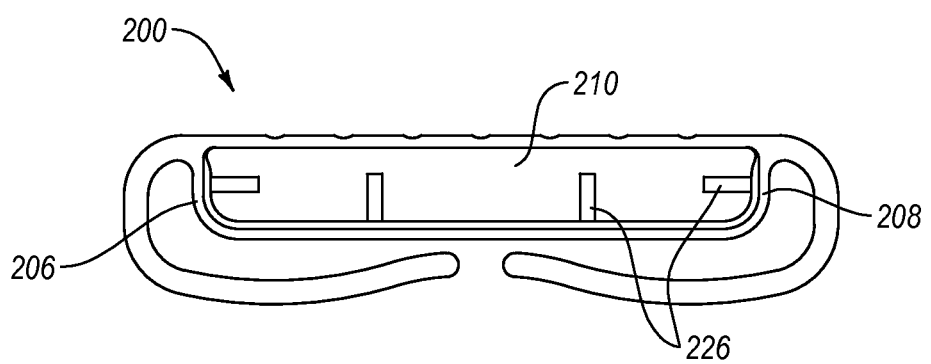

In the embodiment illustrated in FIGS. 2A and 2B, a wearable housing 200 includes one or more support fins 226. In some embodiments, support fins 226 may be disposed on one or more of the back wall (not shown), first side wall 206, second sidewall 208, outer wall 202, and/or inner wall 204, and may extend a distance into the substantially hollow receptacle area 210. The support fins 226 may be utilized to position and/or secure a magnet within the substantially hollow receptacle area 210 (see also FIGS. 3A-3C and discussion thereof). The support fins 226 may be disposed longitudinally, transversely, diagonally, circularly, in a curved path, or may have portions running in one direction and other portions running in another direction. Additionally, or alternatively, some support fins 226 may run in one direction or combination of directions while other support fins 226 run in another direction or combination of directions. One of skill in the art will understand that any number of support fins 226 may be used in any combination to position a magnet within a substantially hollow receptacle area 210.

Figure 3A:
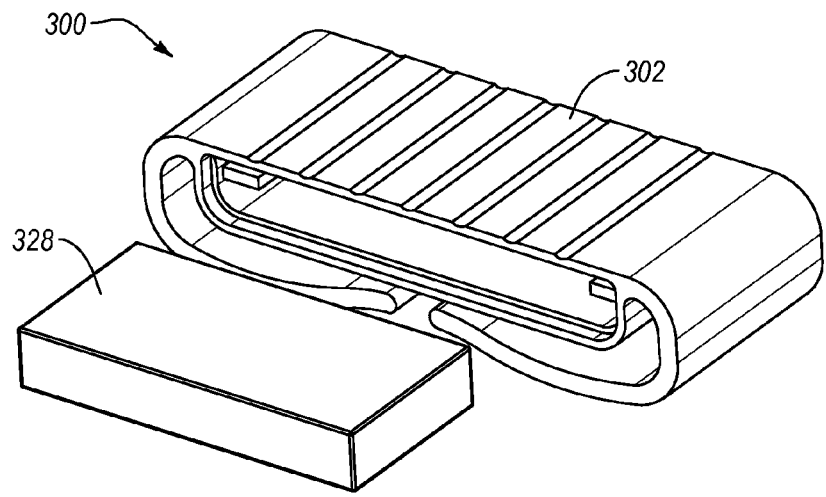
FIGS. 3A-3C illustrate a wearable housing and a magnet, and the positioning of the magnet within a substantially hollow receptacle area of the wearable housing.
Figure 3B:
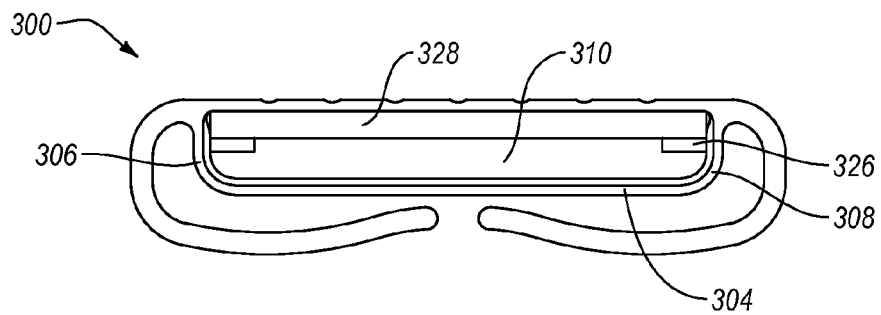
Figure 3C:
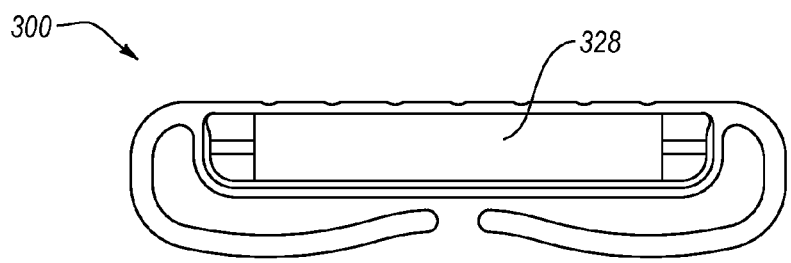

FIGS. 3A-3C illustrate an embodiment of a wearable housing 300 including a magnet 328. As shown in the figures, a magnet 328 may be positioned within or partially within a substantially hollow receptacle area 310. The magnet 328 and/or substantially hollow receptacle area 310 may be configured in size and shape so that the magnet 328 fits securely within the substantially hollow receptacle area 310. For example, the magnet 328 may be positioned within the substantially hollow receptacle area 310 such that the magnet 328 abuts against one or more support fins 326, as shown in FIGS. 3B and 3C.

The support fins 326 may aid in securely positioning the magnet 328 within the substantially hollow receptacle area 310 by maintaining the magnet 328 at a desired location within the substantially hollow receptacle area 310. For example, support fins 326 may secure the magnet 328 against the outer wall 302. Additionally, or alternatively, support fins 326 may secure the magnet against the first sidewall 306, second sidewall 308, inner wall 304, back wall (not shown), and/or another support fin or support fins 326.

As illustrated in FIGS. 3A-3C, the magnet 328 and/or substantially hollow receptacle area 310 may be configured in size and shape so that the magnet 328 fills a portion of the volume of the substantially hollow receptacle area 310. For example, the magnet 310 may fill 10% or less of the volume. In other embodiments, the magnet may fill more than 10% of the volume, such as between 10-25%, or 25-50%, or 50-75%. In other embodiments, the magnet may fill substantially all of the volume of the substantially hollow receptacle area 310, such as 75-100% of the volume. In such an embodiment, the wearable housing 300 may not include support fins, and the magnet 328 may abut and be secured in position by the outer wall 302, the first sidewall 306, second sidewall 308, the inner wall 304 and the back wall.

In some embodiments, the magnet 328 and/or substantially hollow receptacle area 310 may be configured in size and shape such that the magnet 328 is completely contained within the substantially hollow receptacle area 310 during use. In other embodiments, a portion or portions of the magnet 328 may reside outside of the substantially hollow receptacle area 310. For example, in some embodiments, a portion of the magnet 328 may protrude out of an opening of the substantially hollow receptacle area 310 on one side or end of the wearable housing 300. In another example, a portion of the magnet 328 may protrude out of an opening of the substantially hollow receptacle area 310 on two sides or ends of the wearable housing 300 (e.g., in embodiments of a wearable housing not exhibiting a back wall).

While the support fins described above can help secure the magnet(s) in place, it will be appreciated that other securing means can also be used, such as adhesives and friction fits between the interior surfaces of the housing.

The magnet 328 may be formed of any material capable of exhibiting a magnetic force (e.g., a permanent magnet). In some embodiments, the magnet 328 may be a rare-earth magnet, such as, but not limited to neodymium magnets (i.e., neodymium-iron-boron magnets) and samarium-cobalt magnets. In some embodiments, the size and grade of the magnet 328 is sufficient to create a pull force of greater than 0.25 lbs or, even more preferably, greater than 0.5 lb. In other embodiments, the size and grade of the magnet 328 is sufficient to create a pull force of greater than about 1.0 lb., and even more preferably greater than about 2 lbs. In other embodiments, the size and grade of the magnet 328 is sufficient to create a pull force of between about 2 lbs. and about 10 lbs. In other embodiments, the size and grade of the magnet 328 is sufficient to create a pull force of greater than about 5 lbs., such as more than about 10 lbs. or even more than about 20 lbs. In some particular embodiments, the size and grade of the magnet 328 is sufficient to create a pull force of between about 20 lbs. and about 35 lbs., between about 35 lbs. and 50 lbs., and even more particularly greater than about 50 lbs.

Figure 4A:
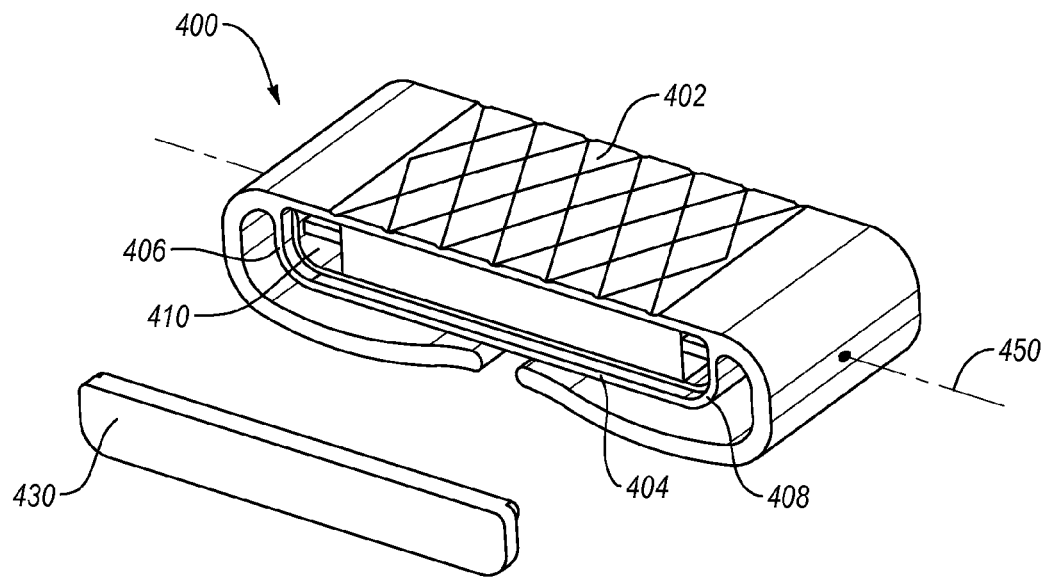
FIGS. 4A and 4B illustrate a wearable housing and a cap and a detachable cap.
Figure 4B:
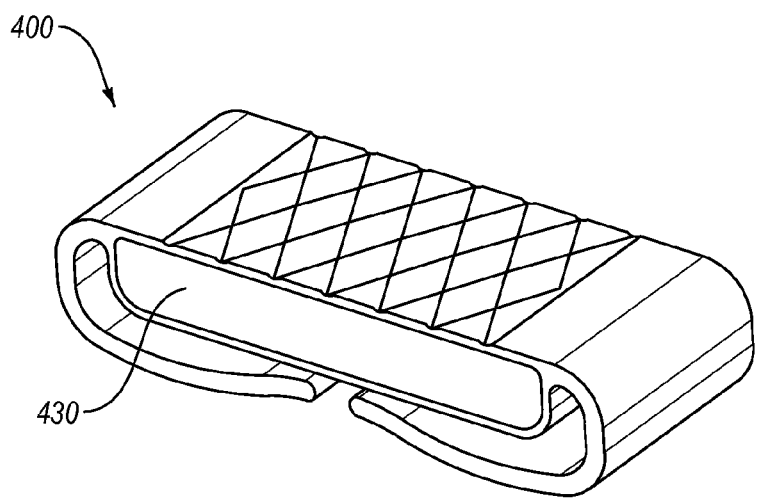

FIGS. 4A and 4B illustrate an embodiment of a wearable housing 400 including a cap 430. The cap 430 may be configured to be detachably connected to the first sidewall 406, second sidewall 408, outer wall 402, and inner wall 404 on a side/end of the wearable housing 400 opposite the back wall (not shown). The cap 430 may thereby further enclose the substantially hollow receptacle area 410 at a second end of the substantially hollow receptacle area 410. The cap 430 may be substantially flat, as in FIGS. 4A and 4B, or may include additional vertices and/or include curved portions.

In some embodiments, the cap 430 may be attached to the wearable housing 400 by configuring the cap 430 to fit securely within a portion of the substantially hollow receptacle area 410. For example, the cap 430 may be configured to fit within the portion of the substantially hollow receptacle area 410 proximate the second end of the substantially hollow receptacle area 410. In some embodiments, the wearable housing 400 may include a countersink disposed along the outer wall 402, inner wall 404, first sidewall 406, and/or second sidewall 408, or portions thereof. The countersink portion may aid in positioning and securing the cap 430 on the wearable housing 400 at the opening (i.e., at the second end of the substantially hollow receptacle area 410).

In other embodiments, at least a portion of the cap 430 may be attached or integrally connected to another portion of the wearable housing 400. For example, the cap 430 may include a tab or hinge (not presently shown) connecting the cap to another portion (e.g., the outer wall 402, inner wall 404, first sidewall 406, and/or second sidewall 408) of the wearable housing 400. In these embodiments, the tab or hinge may keep the cap 430 attached to the remainder of the wearable housing 400 even when the cap 430 is not positioned to enclose the second end of the substantially hollow receptacle area 410. In these embodiments, a cap 430 may be detached or disengaged from the housing (e.g., to gain access to the substantially hollow receptacle area 410), but not completely detached from the remainder of the wearable housing 400. For example, the cap 430 may be detached or disengaged from enclosing the substantially hollow receptacle area 410 by folding it up, down, or sideways along a tab or hinge connecting the cap 430 to the wearable housing 400. In other embodiments, the cap 430 may be integrally formed with the remainder of the wearable housing 400, such that it is not detachable.

The cap 430 can also be integrally attached to the housing by sonic welding, by chemical adhesives or other fastening means.

Figure 5:
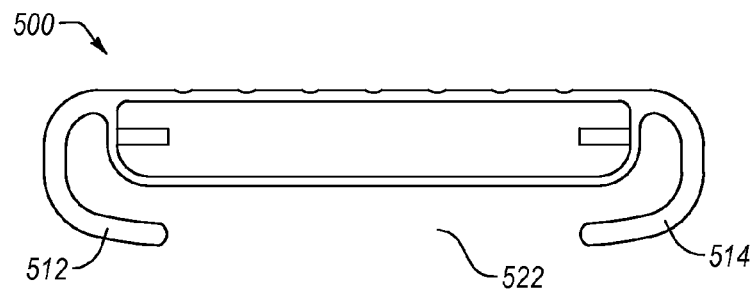
FIGS. 5 and 6 illustrate embodiments of wearable housings including clasping members of various sizes and shapes.

FIGS. 5-8 illustrate other wearable housing embodiments with a variety of clasping member and/or slot variations. FIG. 5 illustrates a wearable hosing 500 including a first clasping member 512 and a second clasping member 514. In this embodiment, the first clasping member 512 and the second clasping member 514 have terminating ends that do not coincide or abut one another, leaving a gap 522. Likewise, in the embodiment shown in FIG. 6, a wearable housing 600 includes a first clasping member 612 and a second clasping member 614 with terminating ends that do not coincide or abut one another, leaving a gap 622. However, gap 622 is significantly smaller than the gap 522 of FIG. 5. The gap 522 can be larger when the clasping members 512 and 514 are sufficiently rigid to remain attached to a sufficiently rigid strap or belt. However, when the strap and/or the clasping members are relatively more flexible, it is desirable to provide longer clasping members that are capable of remaining attached to the strap.

Figure 6:
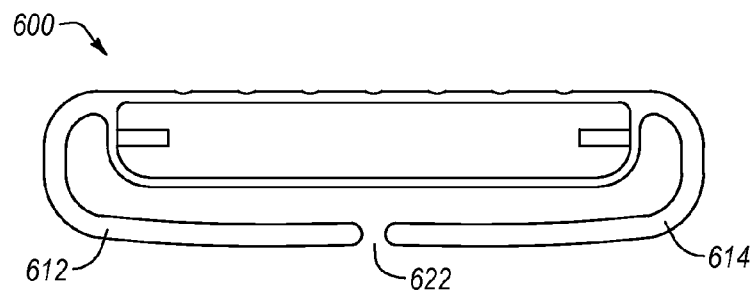

The embodiments illustrated in FIGS. 5 and 6 show that the clasping members may be configured in a variety of different sizes and shapes. For example, a gap 522 or 622 may be relatively wide or narrow, depending on the configuration of the clasping members. Likewise, a gap 522 or 622 may be symmetrically positioned relative to a centerline of the housing (such as shown with regard to centerline 450 of FIGS. 4A and 4B).

In some embodiments, the opposing clasping members are the same length. In other embodiments, one of the clasping members is longer than the opposing clasping member, such that the center of the gap is longitudinally offset from the center of the housing.

In the embodiments shown in FIGS. 5 and 6, the clasping members (512, 514, 612 and 614) have a uniform thickness. In other embodiments, clasping members may have a thickness that is non-uniform. For example, one or more clasping members may have a thickness that tapers and/or expands in one direction or the other.

Figure 7:
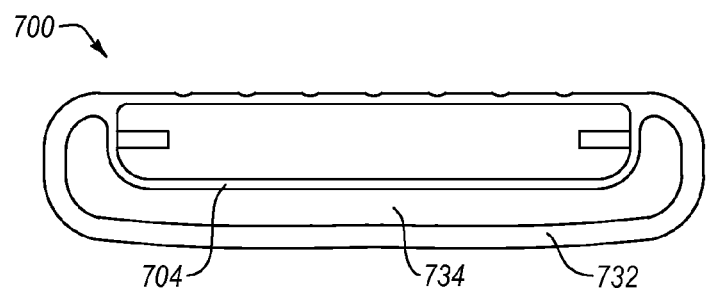
FIG. 7 illustrates a wearable housing including an enclosed loop and an enclosed slot formed by connected clasp members.

FIG. 7 illustrates an embodiment of a wearable housing 700 including an enclosed loop 732 that is formed by two clasping members being integrally connected (with no terminating ends). The enclosed loop 732 forms an enclosed slot 734 defined by the area between the enclosed loop 732 and the exterior surface of the inner wall 704. In this particular embodiment, the wearable housing 700 may be attached to a strap (not shown) by positioning the strap through the enclosed slot 734. As with the other embodiments including one or more clasping members, an enclosed loop may have a uniform or non-uniform thickness, and may be substantially straight or may include one or more curved or arcuate portions. Additionally, the enclosed loop 732 may be configured to flex and apply a friction force with strap to securely engage the wearable housing 700 in a desired positioning on the strap. Or, alternatively, the enclosed loop can be configured with sufficient spacing and rigidity that it does not flex to allow the housing to be moved along the strap.

Figure 8:
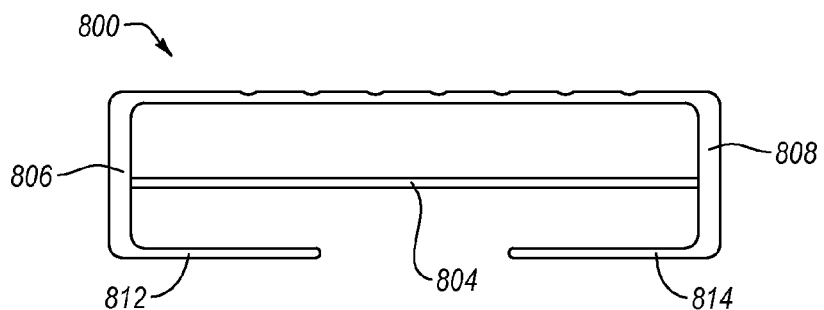
FIG. 8 illustrates another embodiment of a wearable housing with clasping members extending directly away from sidewalls.

FIG. 8 illustrates another embodiment of a wearable housing 800 including a first clasping member 812 and a second clasping member 814. In the embodiment shown in FIG. 8, the first clasping member 812 protrudes laterally directly down from the first sidewall 806 and the second clasping member 814 protrudes laterally down from the second sidewall 808, parallel to the first clasping member and perpendicular to the outer and inner walls. Both of the first clasping member 812 and the second clasping member 814 extend to a terminating ends adjacent to the exterior surface of the inner wall 804.

In other embodiments, the one or more clasping members protrude longitudinally away from the outer walls parallel to the outer and inner walls (see, e.g., FIGS. 5-7), and in yet other embodiments, one or more clasping members may be disposed from the inner wall.

Figure 9A:
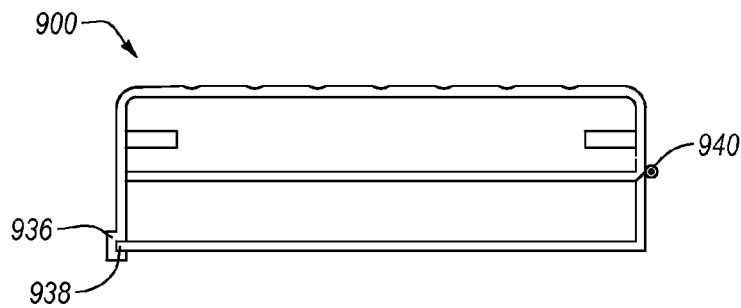
FIGS. 9A-9C illustrate a wearable housing with clasping members including hinging and locking elements.
Figure 9B:
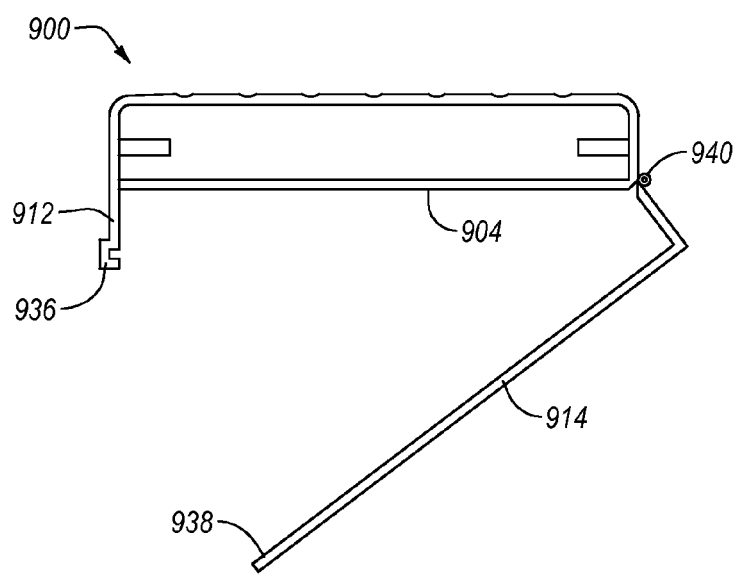
Figure 9C:
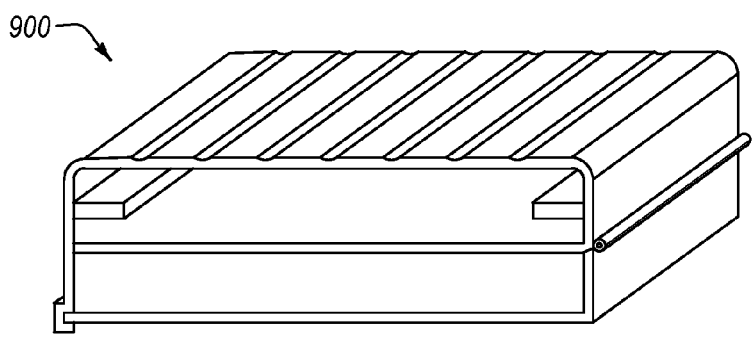

FIGS. 9A-9C illustrate another embodiment of a wearable housing 900 including a first clasping member 912 and a second clasping member 914 that extend to terminal ends that coincide and abut each other at the same location to form an enclosed loop. In the embodiment shown in FIGS. 9A-9C, the first clasping member 912 also includes a first locking element 936, and the second clasping member 914 includes a second locking element 938. The first locking element 936 and the second locking element 938 may be configured to detachably connect or engage with each other when the first and second clasping members are connected to form the closed loop.

In some embodiments, the wearable housing also includes a clasping member hinge 940 configured to allow a clasping member to turn on the clasping member hinge 940 as the first locking element 936 and the second locking element 938 detach and disengage from each other to open the closed loop and re-separate the first clasping member 912 and second clasping member 914. The hinge 940 can be composed of a plurality of hinge elements enabling rotation about a central axis. Alternatively, the hinge can be composed of a recessed portion of the material between the sidewall and the clasping member, which is thin enough to enable the clasping member to flex about the recessed portion.

Figure 10A:
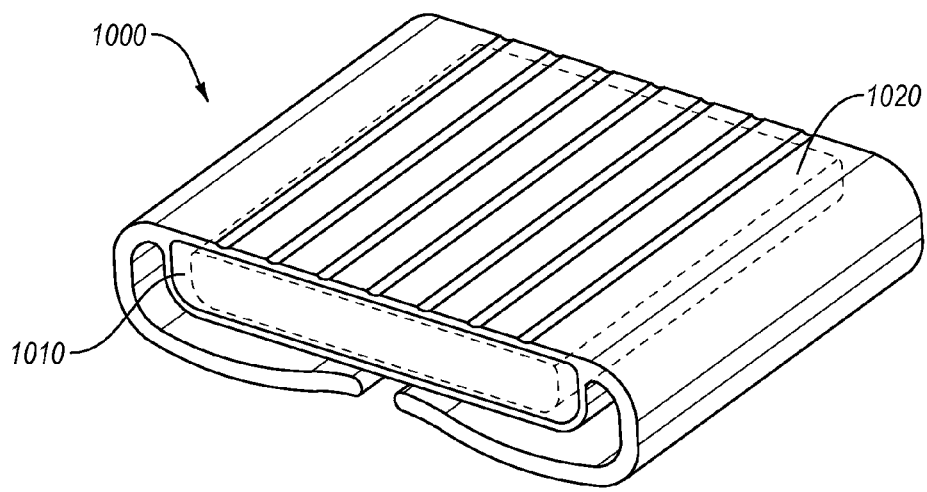
FIGS. 10A-10C illustrate embodiments of wearable housings including enlarged and a plurality of receptacle areas.
Figure 10B:
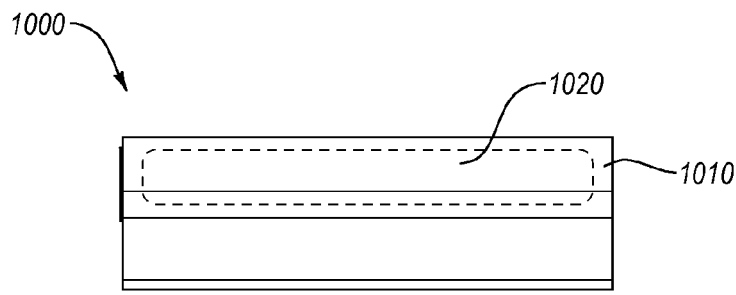
Figure 10C:
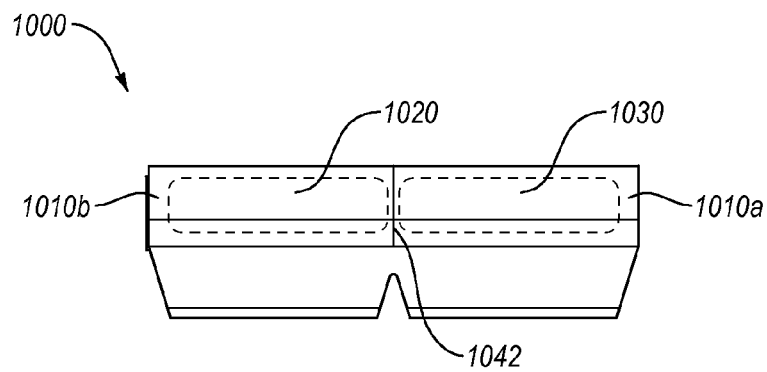

FIGS. 10A-10C illustrate another embodiment of a wearable housing 1000 including an extended or enlarged receptacle area 1010. The wearable housing 1000 may, for example, be configured in size and shape to hold two or more magnets within the substantially hollow magnetic receptacle area 1010. For example, two or more magnets can be positioned side by side within the substantially hollow receptacle area 1010. Alternatively, a single enlarged magnet can be positioned within the receptacle area 1010.

As described herein, the wearable housing 1000 is configured to hold any quantity and size of magnets to provide the desired amount of magnetic holding force (e.g., 2+lbs) at the surface area of the outer wall to hold the tools or objects positioned there.

As shown in the embodiment illustrated by FIG. 10C, a wearable housing 1000 may also include one or more partitions 1042 configured to divide the substantially hollow receptacle area into one or more receptacle areas (1010a and 1010b), and one or more magnets (1020 and 1030) may then be positioned within each of the one or more receptacle areas, respectively. The partition 1042 may be substantially straight, or may include vertices and/or curved or arcuate portions. The partition 1042 can extend completely or only partially between the outer and inner sidewalls.

The embodiments of FIGS. 10A-10C show the housing to be relatively wider than in the other embodiments. It will be appreciated, however, that the overall width of the housing can vary to accommodate any need or preference. Accordingly, the width can vary from less than 0.5 inches to more than three inches. Similarly, the height of the housing can also vary to accommodate different needs and preferences, including the need to accommodate different sized straps and belts. Accordingly, the height can vary from less than 0.05 inches to more than four inches. Although, in some embodiments, the height is between about one inch and three inches.

In some embodiments, the height of the housing is greater than the width of the housing. In other embodiments, the width is greater than the height.

In some embodiments, the wearable housing is configured for modular functionality, such that a plurality of separate wearable housings can be positioned on a single belt or strap, including MOLLE strapping.

The embodiment illustrated in FIG. 11 includes a wearable housing 1100 attached to a strap 1120. The embodiment illustrated in FIG. 11 shows that a utility item, such as a handgun 1144, can be selectably attached to the wearable housing 1100. For example, the utility item 1144 (or two or more such utility items) may be detachably secured against the outer wall 1102 of the wearable housing by the magnetic force of the magnet(s) positioned within the wearable housing 1100. While the present example illustrates that a handgun 1144 can be attached to and held in place against the wearable housing 1100, it will be appreciated that other utility items can also be used, so long as they are ferrous or exhibit characteristics of magnetic attraction. For example, the utility item 1144 can also comprise a handheld tool (e.g., hammer, wrench, screwdriver, tape measurer, level, etc.), hardware (e.g., nails, screws, rivets, etc.), flashlight, or other handheld or hand manipulated item capable of magnetic attraction.

It will be appreciated from the foregoing, that the wearable housing is capable of providing many advantages over existing holsters and containers known in the prior art. Among other things, the present invention provides a mechanism that is capable of selectably securing one or more items in an accessible position that might not be as accessible with a traditional holster or container, thereby overcoming some of the difficulty that could otherwise be required to open the container or holster. This advantage is particularly apparent when considering circumstances in which only a single hand is available, such as during many tool operations or during one-handed drawing, shooting, and reloading of a handgun.

The present invention may be embodied in other specific forms without departing from its spirit or essential characteristics. The described embodiments are to be considered in all respects only as illustrative and not restrictive. In fact, any combination of the features disclosed in any of the foregoing embodiments can be combined. The invention can incorporate any combination of the different features described herein, such that components and elements from one embodiment can be incorporated into or replace elements from any of the other embodiments described herein.

What is claimed is:

1. A wearable housing configured in size and shape for housing a magnet and configured to be selectably connected to a wearable strap, the wearable housing comprising:
    an outer wall extending from a first end to a second end of the outer wall along a longitudinal axis, the outer wall comprising a first exterior surface and a first interior surface that each extend between the first end and the second end of the outer wall;
    an inner wall extending from a first end to a second end of the inner wall along the longitudinal axis, the inner wall comprising a second exterior surface and a second interior surface that each extend between the first end and the second end of the inner wall;
    a first sidewall positioned at and connecting the first end of the outer wall to the first end of the inner wall;
    a second sidewall positioned at and connecting the second end of the outer wall to the second end of the inner wall; the first and second sidewalls connecting the outer wall a predetermined distance from the inner wall, thereby defining a substantially hollow receptacle area between the outer wall and the inner wall and between the first and second sidewalls, the outer wall, inner wall, and first and second side walls also defining at least one opening providing access to the substantially hollow receptacle area, the at least one opening being disposed between the outer wall and inner wall and between the first and second side was and facing a direction perpendicular to the longitudinal axis;
    a first clasping member disposed proximate the first end of the outer wall, the first clasping member being connected to at least one of the first end of the outer wall or the first sidewall, the first clasping member extending around to the inner wall to a first location adjacent to the second exterior surface, thereby forming a first slot defined by an area between the first clasping member and the second exterior surface; and
    a second clasping member disposed proximate the second end of the outer wall, the second clasping member being connected to at least one of the second end of the outer wall or the first sidewall, the second clasping member extending around to the inner wall to a second location adjacent to the second exterior surface, thereby forming a second slot defined by an area between the second clasping member and the second exterior surface,
    wherein the outer and inner walls have lengths along the longitudinal axis that are longer than widths perpendicular to the longitudinal axis; and
    a magnet, the magnet being positioned within the substantially hollow receptacle area.

2. The wearable housing of claim 1, further comprising a back wall connected to each of the first side wall, the second side wall, the outer wall and the inner wall, thereby enclosing a first end of the substantially hollow receptacle area opposite the at least one opening.

3. The wearable housing of claim 2, further comprising a cap connected to each of the first sidewall, the second side wall, the outer wall and the inner wall, thereby enclosing a second end of the substantially hollow receptacle area.

4. The wearable housing of claim 3, wherein the cap is detachably connected to the housing at the second housing side.

5. The wearable housing of claim 1, wherein the magnet is securely positioned directly against the first interior surface within the substantially hollow receptacle area.

6. The wearable housing of claim 1, wherein the wearable housing further comprises a first support fin disposed at the first sidewall, second sidewall, outer wall, or inner wall and extending into the substantially hollow receptacle area.

7. The wearable housing of claim 6, the magnet being positioned within the substantially hollow receptacle area directly abutting the first support fin.

8. The wearable housing of claim 7, further comprising two or more support fins disposed at the first sidewall, second sidewall, outer wall, or inner wall, and extending into the substantially hollow receptacle area.

9. The wearable housing of claim 1, wherein the first clasping member and the second clasping member extend to terminating ends that do not coincide or abut each other, thereby leaving a gap between the terminating ends.

10. The wearable housing of claim 1, wherein the first location is the same as the second location, and wherein the first clasping member and the second clasping member are connected directly together to form a closed loop containing the first and second slots.

11. The wearable housing of claim 10, wherein the first clasp further comprises a first locking element and the second clasp further comprises a second locking element, the first locking element and the second locking element configured to detachably connect with each other when the first and second clasping members are connected to form the closed loop.

12. The wearable housing of claim 1, wherein the first exterior surface comprises a textured pattern formed by one or more grooves or projections formed on the outer wall.

13. The wearable housing of claim 1, wherein the wearable housing further includes at least two magnets positioned within the substantially hollow receptacle area.

14. The wearable housing of claim 13, further comprising a partition that is disposed within the substantially hollow receptacle area, thereby dividing the substantially hollow receptacle area into a first magnet receptacle and a second magnet receptacle, the at least two magnets including a first magnet contained in the first magnet receptacle and a second magnet contained in the second magnet receptacle.

15. A wearable housing configured in size and shape for housing a magnet and configured to be selectably connected to a wearable strap, the wearable housing comprising:
　an outer wall extending from a first end to a second end of the outer wall, the outer wall comprising a first exterior surface and a first interior surface that each extend between the first end and the second end of the outer wall;
　an inner wall extending from a first end to a second end of the inner wall, the inner wall comprising a second exterior surface and a second interior surface that each extend between the first end and the second end of the inner wall;
　a first sidewall positioned at and connecting the first end of the outer wall to the first end of the inner wall;
　a second sidewall positioned at and connecting the second end of the outer wall to the second end of the inner wall;
　the first and second sidewalls connecting the outer wall a predetermined distance from the inner wall, thereby defining a substantially hollow receptacle area between the outer wall, the inner wall and the first and second sidewalls;
　a first clasping member joined to the first end of the outer wall and extending downwardly around the first sidewall leaving a space between the first clasping member and at least a portion of the first sidewall, the first clasping member extending to the inner wall and terminating at a first location adjacent to the second exterior surface, thereby forming a first slot defined by an area between the first clasping member and the second exterior surface;
　a second clasping member joined to the second end of the outer wall and extending downwardly around the second sidewall leaving a space between the second clasping member and at least a portion of the second sidewall, the second clasping member extending to the inner wall and terminating at a second location adjacent to the second exterior surface, thereby forming a second slot defined by an area between the second clasping member and the second exterior surface, and thereby forming a gap between terminating ends of the first and second clasping members; and
　a magnet, the magnet being positioned within the substantially hollow receptacle area,
　wherein the first and second slots defined by the first and second clasping members are configured for engaging a strap between the second exterior surface and the first and second clasping members such that the wearable housing is securable upon the strap while the gap is maintained, and
　wherein the terminating ends of the first and second clasping members extend closer to the second exterior surface than portions of the first and second clasping members adjacent to the terminating ends.

16. The wearable housing of claim 15, further comprising a handgun directly biased against the first exterior surface and held in place by the magnetic association between the handgun and the magnet.

17. A wearable housing configured in size and shape for housing a magnet and configured to be selectably connected to a wearable strap, the wearable housing comprising:
　an outer wall extending from a first end to a second end of the outer wall, the outer wall comprising a first exterior surface and a first interior surface that each extend between the first end and the second end of the outer wall;
　an inner wall extending from a first end to a second end of the inner wall, the inner wall comprising a second exterior surface and a second interior surface that each extend between the first end and the second end of the inner wall;
　a first sidewall positioned at and connecting the first end of the outer wall to the first end of the inner wall;
　a second sidewall positioned at and connecting the second end of the outer wall to the second end of the inner wall;
　the first and second sidewalls connecting the outer wall a predetermined distance from the inner wall, thereby defining a substantially hollow receptacle area between the outer wall, the inner wall and the first and second sidewalls;
　a first clasping member disposed proximate the first end of the outer wall, the first clasping member being connected to at least one of the first end of the outer wall or the first sidewall, the first clasping member extending around the inner wall to a first location adjacent to the second exterior surface, thereby forming a first slot defined by an area between the first clasping member and the second exterior surface;
　a second clasping member disposed proximate the second end of the outer wall, the second clasping member being connected to at least one of the second end of the outer wall or the first sidewall, the second clasping member extending around the inner wall to a second location adjacent to the second exterior surface, thereby forming a second slot defined by an area between the second clasping member and the second exterior surface;

a magnet, the magnet being positioned within the substantially hollow receptacle area; and one or more support fins disposed at the first sidewall, second sidewall, outer wall, or inner wall and extending into the substantially hollow receptacle area.

18. The wearable housing of claim 17, further comprising a back wall connected to each of the first side wall, the second side wall, the outer wall and the inner wall, thereby encasing a first end of the substantially hollow receptacle area, and further comprising a cap connected to each of the first side wall, the second side wall, the outer wall and the inner wall, thereby encasing a second end of the substantially hollow receptacle area.

* * * * *